United States Patent
Tohmeh

(10) Patent No.: US 9,561,059 B1
(45) Date of Patent: Feb. 7, 2017

(54) MINIMALLY INVASIVE FACET RELEASE

(71) Applicant: NuVasive, Inc., San Diego, CA (US)

(72) Inventor: Antoine Tohmeh, Spokane, WA (US)

(73) Assignee: NUVASIVE, Inc., San Diego, CA (US)

( * ) Notice: Subject to any disclaimer, the term of this patent is extended or adjusted under 35 U.S.C. 154(b) by 24 days.

(21) Appl. No.: 13/684,492

(22) Filed: Nov. 23, 2012

Related U.S. Application Data

(60) Provisional application No. 61/563,240, filed on Nov. 23, 2011.

(51) Int. Cl.
*A61B 17/70* (2006.01)

(52) U.S. Cl.
CPC ............... *A61B 17/7064* (2013.01)

(58) Field of Classification Search
CPC ............ A61B 17/7062–17/707; A61B 17/7074–17/708; A61B 17/7083–17/7085; A61B 17/70–17/7092
USPC ........................ 606/86 A, 246–279
See application file for complete search history.

(56) References Cited

U.S. PATENT DOCUMENTS

| | | | |
|---|---|---|---|
| 5,762,629 A | 6/1998 | Kambin | |
| 5,910,134 A | 6/1999 | Fussman | |
| 6,277,094 B1 | 8/2001 | Schendel | |
| 6,398,811 B1 | 6/2002 | McKay | |
| 6,506,151 B2 | 1/2003 | Estes | |
| 6,520,907 B1 | 2/2003 | Foley | |
| 6,648,895 B2 | 11/2003 | Burkus | |
| 6,867,247 B2 | 3/2005 | Williams | |
| 6,916,330 B2 | 7/2005 | Simonson | |
| 6,929,606 B2 | 8/2005 | Ritland | |
| 7,118,598 B2 | 10/2006 | Michelson | |
| 7,198,598 B2 | 4/2007 | Smith | |
| 7,244,258 B2 | 7/2007 | Burkus | |
| 7,320,688 B2 | 1/2008 | Foley | |
| 7,588,588 B2 | 9/2009 | Spitler | |
| 7,608,094 B2 | 10/2009 | Falahee | |
| 7,824,429 B2 | 11/2010 | Culbert | |
| 7,837,713 B2 | 11/2010 | Petersen | |
| 7,892,238 B2 * | 2/2011 | DiPoto et al. .............. 606/86 A |
| 7,959,564 B2 | 6/2011 | Ritland | |
| 7,993,378 B2 | 8/2011 | Foley | |
| 8,016,767 B2 | 9/2011 | Miles | |
| 8,021,392 B2 | 9/2011 | Petersen | |
| 8,105,361 B2 | 1/2012 | Anderson | |
| 8,641,733 B2 | 2/2014 | Chin | |

(Continued)

FOREIGN PATENT DOCUMENTS

JP   11290337 A   10/1999
KR   20100123083 A   11/2010

(Continued)

*Primary Examiner* — Jan Christopher Merene
*Assistant Examiner* — Steven Cotroneo
(74) *Attorney, Agent, or Firm* — Bradley Arant Boult Cummings LLP

(57) ABSTRACT

Minimally invasive facet release is performed during spine surgery. The minimally invasive facet release may be performed at a single level or over multiple levels. The minimally invasive facet release may be performed through a working corridor instrument which may be a tissue retractor or an access tube. When coupled with a minimally invasive pedicle screw fixation system, the facet release methods described enable a surgeon to correct a wide array of spinal deformities in a purely minimally invasive fashion.

6 Claims, 7 Drawing Sheets

(56) References Cited

U.S. PATENT DOCUMENTS

| | | | |
|---|---|---|---|
| 2004/0006391 A1 | 1/2004 | Reiley | |
| 2005/0065608 A1 | 3/2005 | Michelson | |
| 2006/0030850 A1* | 2/2006 | Keegan | A61B 17/0293 606/60 |
| 2007/0173831 A1* | 7/2007 | Abdou | 606/61 |
| 2007/0233079 A1* | 10/2007 | Fallin et al. | 606/61 |
| 2008/0077152 A1 | 3/2008 | McClintock | |
| 2009/0171394 A1* | 7/2009 | Abdou | 606/247 |
| 2009/0254131 A1* | 10/2009 | Roh | 606/86 A |
| 2009/0270902 A1 | 10/2009 | Assell | |
| 2010/0106194 A1 | 4/2010 | Bonutti | |
| 2010/0222824 A1* | 9/2010 | Simonson | 606/279 |
| 2010/0280555 A1 | 11/2010 | Aflatoon | |
| 2010/0331891 A1 | 12/2010 | Culbert | |
| 2011/0060366 A1 | 3/2011 | Heim | |
| 2011/0077685 A1 | 3/2011 | Carls | |
| 2011/0130634 A1 | 6/2011 | Solitario | |
| 2011/0144687 A1 | 6/2011 | Kleiner | |
| 2011/0208226 A1 | 8/2011 | Fatone | |
| 2011/0288594 A1* | 11/2011 | Woolley et al. | 606/279 |
| 2012/0165873 A1 | 6/2012 | Perez-Cruet | |
| 2013/0053896 A1* | 2/2013 | Voyadzis | 606/279 |
| 2013/0103152 A1 | 4/2013 | Kwon | |
| 2013/0190575 A1* | 7/2013 | Mast et al. | 600/215 |

FOREIGN PATENT DOCUMENTS

| | | |
|---|---|---|
| WO | WO-9740878 A1 | 11/1997 |
| WO | WO-2007120903 A2 | 10/2007 |
| WO | WO-2011044484 A1 | 4/2011 |

* cited by examiner

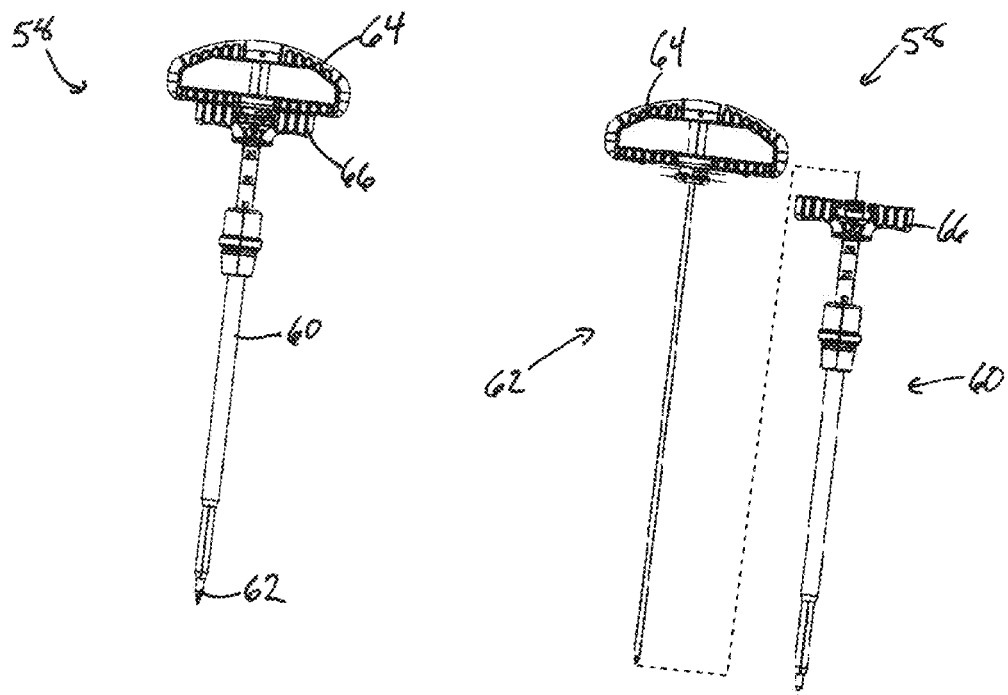
FIG. 10
FIG. 11
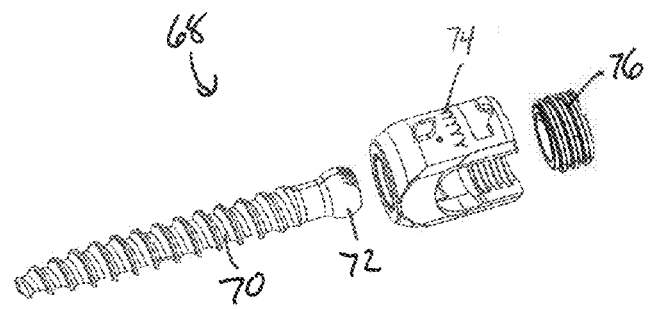
FIG. 12

MINIMALLY INVASIVE FACET RELEASE

CROSS-REFERENCES TO RELATED APPLICATIONS

This application is a non-provisional patent application claiming the benefit of priority from U.S. Provisional Patent Application Ser. No. 61/563,240, filed on Nov. 23, 2011, the entire contents of which is hereby expressly incorporated by reference into this disclosure as if set forth in its entirety herein.

FIELD

This application describes methods and tools for accessing and releasing facet joints during minimally invasive posterior fixation procedures.

BACKGROUND

The spinal column is a highly complex system of bones and connective tissues that provide support for the body and protect the delicate spinal cord and nerves. The anterior side of the spinal column includes a series of vertebral bodies stacked one atop the other. Situated between each vertebral body is an intervertebral disc that cushions and dampens compressive forces exerted upon the spinal column and permits motion between the vertebra. The posterior side of the spinal column includes different bony structures (e.g. lamina, pedicles, transverse processes, spinous processes, facets) that extend from the vertebral bodies and together form an arch around the spinal canal and protect the spinal cord. The adjacent vertebrae are coupled to each other along the posterior column via bilateral facet joints.

There are many types of spinal column disorders including scoliosis (abnormal lateral curvature of the spine), excess kyphosis (abnormal forward curvature of the spine), excess lordosis (abnormal backward curvature of the spine), spondylothesis (forward displacement of one vertebra over another), and other disorders caused by abnormalities, disease or trauma, such as ruptured or slipped discs, degenerative disc disease, fractured vertebra and the like. Patients that suffer from such conditions may experience a wide range of symptoms including, but not limited to, pain (often extreme and debilitating), and diminished nerve function.

To eliminate or reduce the pain associated with the various conditions noted above surgical intervention is often necessary. Often, the goal of the surgical procedure is to reduce impingement of nerves and or the spinal cord by restoring height to disc space, correcting misalignments between the vertebra, and/or correcting instability. Generally the vertebra of the affect motion segments are also fused together to prevent a return to the abnormal state. Spinal fixation systems are often used during the spinal fusion procedures to temporarily eliminate motion and secure a spinal motion segment in place until sufficient bone growth occurs to fuse the vertebrae together. More recently these fixation systems have been deployed through minimally invasive means that allow correction without creating large open exposures. While these spinal fusion procedures and minimally invasive pedicle screw fixations have a high rate of success, many existing surgical techniques are limited by the extent to which they can correct disc height and/or sagittal and/or coronal deformity. In order to achieve the optimal sagittal and/or coronal deformity correction, a facet release coupled with a spinal fixation construct is often necessary. Previous surgical procedures involving a facet release have been done using a midline incision which is dissected away from the spine to expose the facet (e.g. as is done during a posterior lateral interbody fusion PLIF).

The instruments, tools, and techniques described herein are directed towards reducing these challenges and others associated with posterior spinal fixation.

BRIEF DESCRIPTION OF THE FIGURES

Many advantages of the present invention will be apparent to those skilled in the art with a reading of this specification in conjunction with the attached drawings, wherein like reference numerals are applied to like elements and wherein:

FIG. 10 is an enlarged superior view of an axial cross section of the abdomen of a patient in the prone position illustrating the use of a symmetrical sequential dilator set to dilate down to the facet.

FIG. 9 is a superior view of an axial cross section of the abdomen of a patient in the prone position illustrating the use of a tissue retractor to expose the facet.

FIG. 10 is a perspective view of a pedicle access needle according to one example embodiment;

FIG. 11 is a perspective view of the pedicle access needle of FIG. 10, depicting the separation of a stylet component and a cannula component, FIG. 12 is a perspective view of a pedicle screw used for posterior fixation, according to one example embodiment;

DETAILED DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present application describes minimally invasive facet release that may be completed without the extensive muscle dissection, denervation, and blood loss levels presently encountered when facet release is included during a spinal procedure. The minimally invasive facet release is generally performed in conjunction with implantation of a posterior fixation construct and may be performed in addition to other procedures, such as for example, interbody fusion (e.g. lateral interbody fusion or transforaminal interbody fusion (TLIF)). The minimally invasive facet release may be performed during single level and multilevel procedures. The minimally invasive facet release may aid the surgeon in achieving a number of surgical objectives, for example, extra lordosis correction (e.g. correction of a kyphotic deformity), release of the contralateral facet during a TLIF to increase ability to restore disc height, and resection of sagitally oriented facets to restore coronal alignment, minimally disruptive posterior column fusion which could be used to augment minimally disruptive anterior column fusions (e.g., lateral approach fusion procedures) to achieve a minimally disruptive 360 degree fusion, minimally disruptive posterior column fusion without anterior column fusion, among others gains, through one or more small posterior lateral incisions, rather than the typical midline incision (and muscle dissection) typically utilized when facet release is desired. Preferably, the one or more small posterior lateral incisions are the same incisions typically utilized to implant a minimally invasive pedicle screw construct and thus the advantages of the facet release are gained without significantly altering the morbidity of the procedure. Thus, when coupled with a minimally invasive pedicle screw fixation system, the facet release methods described enable a surgeon to correct a wide array of spinal deformities in a purely minimally invasive fashion.

Figure 1:
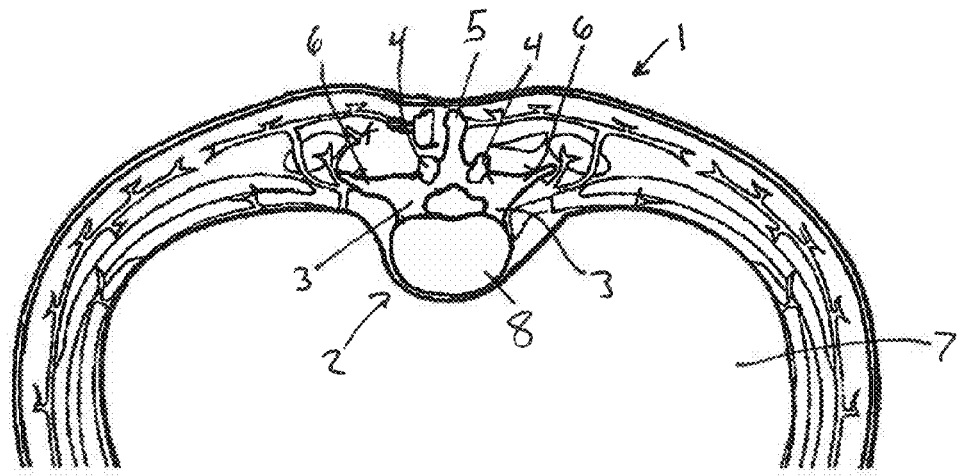
FIG. 1 is a superior view of an axial cross section of the abdomen of a patient in the prone position.
Figure 2:
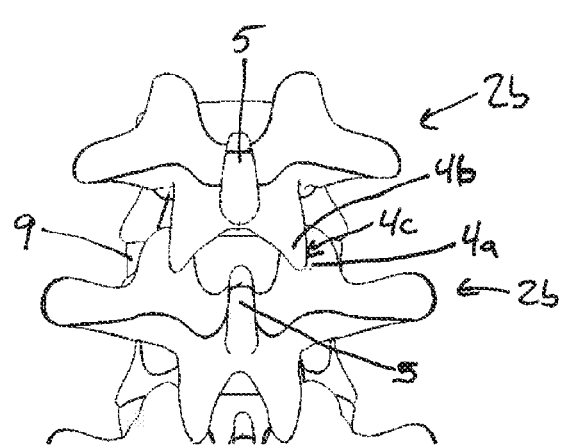
FIG. 2 is a posterior view of two adjacent vertebrae comprising a spinal motion segment.
Figure 3:
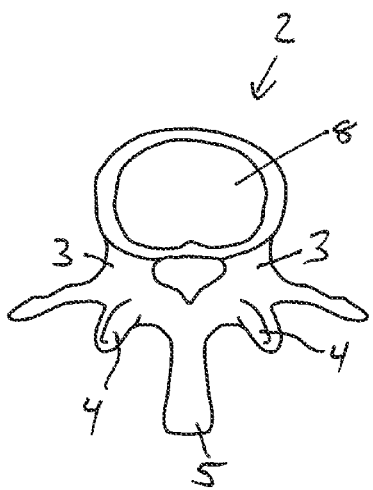
FIG. 3 is a superior view of a vertebra.
Figures 4, 5:
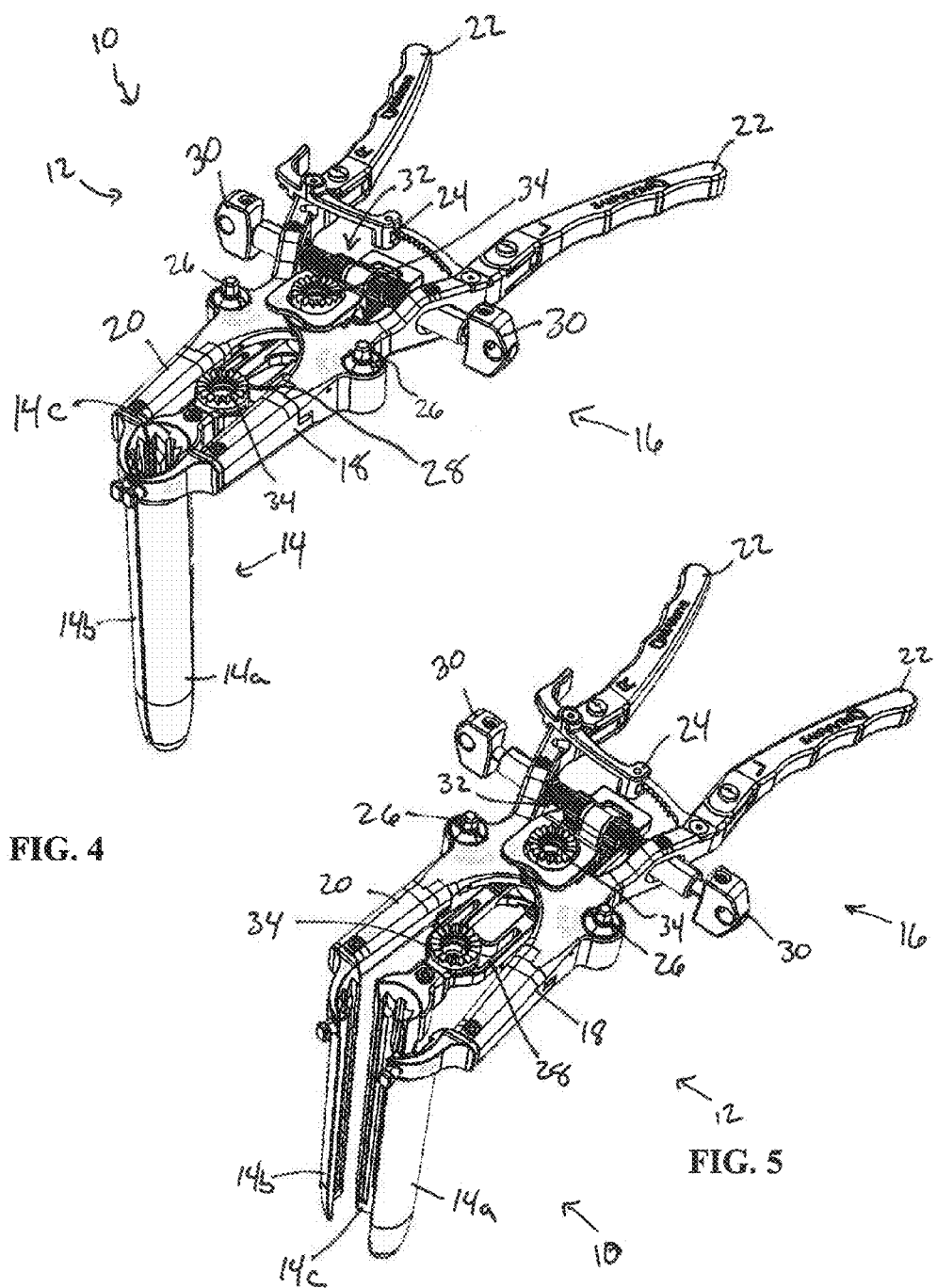
FIG. 4 is a perspective view of a tissue retractor, according to one example embodiment, in first closed position.
FIG. 5 is perspective view of the tissue retractor of FIG. 4, in a second opened position.

FIGS. 1-3 depict the spinal anatomy encountered while performing the minimally invasive facet release described herein. FIG. 1 is a superior view of an axial cross section of the abdomen of a patient in the prone position (that is, lying face down with their back in the air). A vertebra 2 is visible lying below the soft tissue 1 of the patient's back. The vertebral pedicles 3 and half of the facets 4 are visible on either side of the spinous process 5. The vertebral body 8 lies anteriorly against the abdomen 7. Normally, if the facet joints are to be released, the access to the spine will occur through a midline incision over the spinous process 5. The soft tissue 1 is then dissected off the bone and retracted out to the transverse processes 6 to expose the facets and pedicles. FIG. 3 depicts the vertebra 2 of FIG. 1 without the soft tissue 1. FIG. 2 depicts an inferior vertebra 2a and a superior vertebra 2b separated by the intervertebral disc 9, which together form a single motion segment. The facet joint 4c is formed where the superior fact 4a of the inferior vertebra 2a meets the inferior facet 4b of the superior vertebra 2b. The facet capsule is formed of fibrous connective tissue that encases the joint which is lubricated by synovial fluid. Releasing the facet joint involves breaking the connective tissue between the superior facet 4a and inferior facet 4b.

FIGS. 4-12 depict various instruments that are utilized to perform the minimally invasive facet release described herein.

Figure 6:
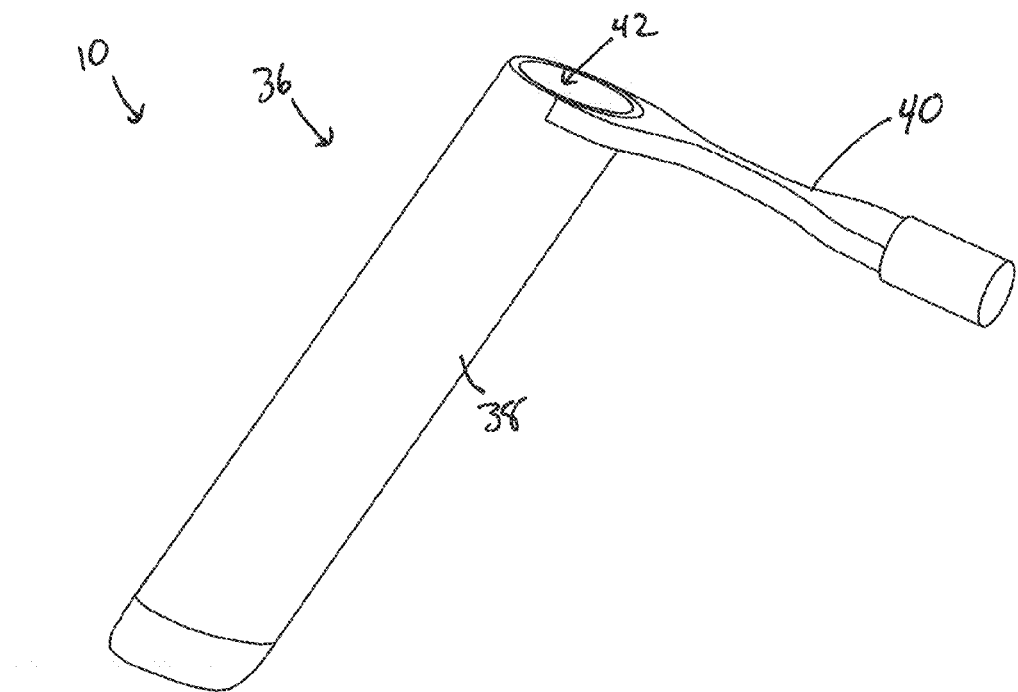
FIG. 6 is a perspective view of an access tube, according to one example embodiment.
Figure 7:
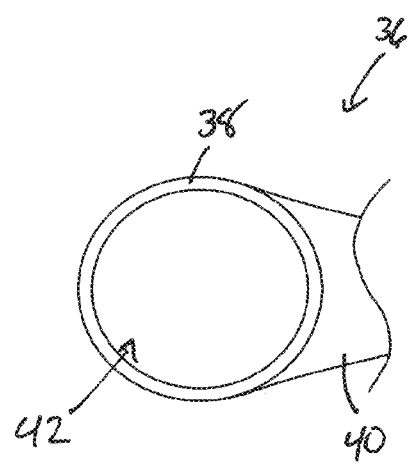
FIG. 7 is a top down view of the access tube of FIG. 6.

Facet release is performed through working corridor instrument 10 that holds back soft tissue and defines an access path (working corridor) from the skin to the spine. The working corridor 10 may be a tissue retractor 12 (FIGS. 4-5) or an access tube 36 (FIGS. 6-7). The example tissue retractor 12 includes a plurality of retractor blades 14 (e.g. blades 14a, 14b, 14c) and a handle 16. The retractor blades are configured to advance through soft tissue in a first position (FIG. 4) configured to minimize tissue disruption during the advance. Thereafter, one or more of the blades 14 may be moved away from the other blade(s) to increase the size of the corridor between them. According to the example embodiment, the handle 16 includes the mechanism(s) that are operated to move the blade(s). For example, the handle 16 includes a first arm 18 pivotally coupled to a second arm 20. The retractor blade 14a is attached to the first arm 18 and the retractor blade 14b is attached to the second arm 20 such that pivoting the first arm 18 relative to the second arm 20 causes blades 14a and 14b to move away from each other. Extensions 22 may be coupled to the first and second arms to facilitate the pivoting action of the arms while lock 24 maintains prevents return movement of the arms. The retractor blades 14a, 14b (or the arms 18, 20 themselves) may also be configured to rotate around the longitudinal axis of the arms 18, 20 to increase the distance between the blades at the distal end adjacent the spine (by way of example, rotation of knobs 26 operate gears (not shown) situated within the arms 18 and 20 which cause a portion of the arms to rotate). The handle also includes a third translating arm 28 attached to the retractor blade 14c which causes the blade 14c to move away from the blades 14a, 14b (by way of example, rotation of knobs 30 operates the rack and pinion gear 32 which translates the translating arm 28). Connection joints 34 may be utilized to mount the tissue retractor 12 to the surgical table with an articulating arm, or other similar mount, if desired. Alternatively, the retractor 12 may be configured to engage a fixation pin or K-wire (not shown) to fix the retractor directly to the spine in a manner less rigid that the connection joint, such that the surgeon may manipulate the angle of the retractor while maintaining the position of the distal. For example, one of blades 14a or 14b may include a channel (not shown) to receive a k-wire (which may be anchored in the lateral aspect of the superior fact of the lower vertebra, a safe zone with no nerves). The k-wire and may include a depth stop to prevent over penetration. A light source may also be connected to the retractor 12 and directed into the working corridor.

The example access tube 36 includes a body 38 and a handle 40. The body 38 surrounds a central lumen 42 that provides the working corridor. The handle 40 facilitates manipulation by the surgeon during insertion and especially, while working through the access tube. Similar to the retractor 12, the access tube 36 may include a connection joint (not shown) for rigid table mounting and a channel (not shown) for receipt of a k-wire (which may be anchored in the lateral aspect of the superior fact of the lower vertebra) to fix the distal end of the tube 36 to the spine while permitting some manipulation of the angle of the working corridor. A light source may also be connected to the access tube 36 and directed into the working corridor.

Figure 8:
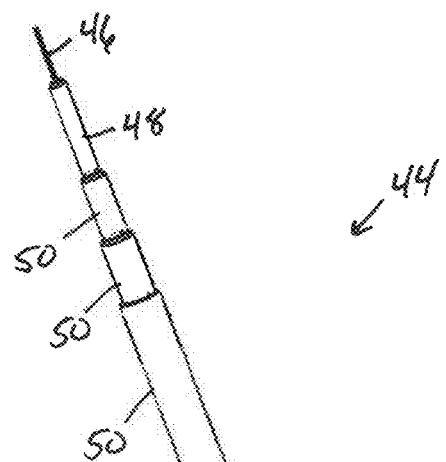
FIG. 8 is a perspective view of a sequential dilation system, according to one example embodiment.

With reference to FIG. 8, a dilation system 44 is illustrated. The dilation system includes a k-wire 46, an initial dilator 48, and at least one additional dilator 50. The dilation system 44 is advanced to the spine ahead of the working corridor instrument 10 to gradually separate the soft tissue and guide the working corridor instrument into position. The K-wire 46 penetrates into the spine (i.e. the pedicle) to anchor the dilation system 44 and also serves as a landmark to orient the surgeon to the position of the facet, adjacent the pedicle. Thereafter the dilators 48 and 50 are sequentially advanced to the spine over the k-wire. The last dilator 50 is dimensioned to slidably receive the retractor blades 14 (in the first position) of the tissue retractor 12 or the body 38 of the access tube 36 thereover. The dilators 48, 50 may preferably be made of a rigid material such as surgical grade metal (e.g., stainless steel or aluminum), surgical-grade, impact resistant plastic, or a combination thereof.

Figure 9:
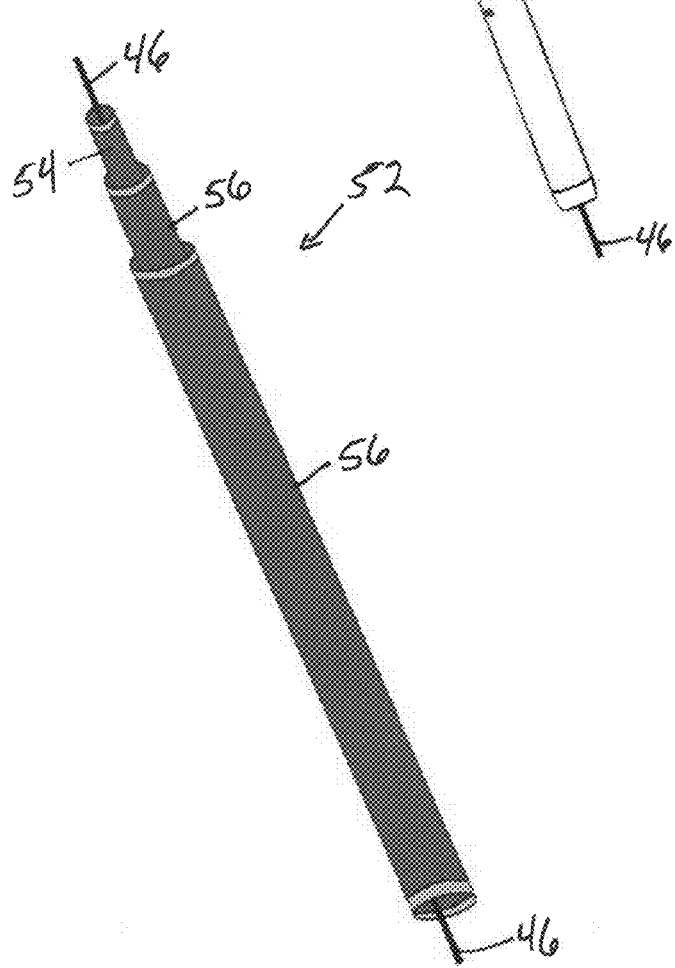
FIG. 9 is a perspective view of a sequential dilation system, according to example embodiment.

With reference to FIG. 9, another dilation system 52 is illustrated. The dilation system 52 is similar to the dilation system 44 except that the dilators (including initial dilator 54 and at least one additional dilator 56) are non-cylindrical. For example, the dilators 54, 56 may be oval in shape, as shown, or oblong, or, the dilators may have an asymmetric shape (e.g. or D-shape). The non-cylindrical shape facilitates dilation of the body tissue in the direction of the facet while minimizing the overall circumference of the tissue expansion necessary. While not show, the body 38 of access tube 36 may be shaped to match the non-cylindrical shape of the dilators of non-cylindrical dilation system 52. Likewise, the tissue retractor 12 may be configured such that the shape of the blades 14 (in the closed position) matches the non-cylindrical dilators. Alternative, the blades 14 may be slightly opened (e.g. the retractor blade 14c may be translated away from arms 14a, 14b) to accommodate the non-cylindrical shape without leaving gaps between the outer dilator 50 and the retractor blades 14.

FIGS. 10-11 illustrate an embodiment of a pedicle access needle 58 that may be used for initial penetration to the spine and placement of the k-wire 44 in the pedicle. The pedicle access needle 58 includes a cannula 60 and a stylet 62. The cannula 60 and stylet 62 may be lockingly mated (e.g. via handle 64 of the stylet and handle 66 of the cannula). Using the handle portions 64 and 66 the pedicle access needle is advanced through a small posteriolateral skin incision, through the soft tissue between the skin and the spine, and positioned on the pedicle (using fluoroscopic guidance to facilitate positioning). Once the access needle 58 is appropriately positioned the needle may be driven into the pedicle to form a pilot hole. With the needle docked in the pedicle, the stylet 62 may be unlocked and removed, leaving the cannula 60 in place. The k-wire 46 of the dilation system 44 (or 52) is then advanced into the pedicle through the cannula 60. When the k-wire is anchored in the pedicle the cannula 60 is removed and sequential dilation is performed over the k-wire.

FIG. 12 illustrates an example pedicle screw 68 that forms part of a posterior fixation construct. The pedicle screw 68 includes a shaft 70 a receiver 74. The shaft 70 anchors into the vertebral body through the pedicle and the receiver 74 receives a fixation rod which is locked in the receiver with a locking cap 76. To form a fixation construct pedicle screws are implanted in at least two vertebrae and connected with the fixation rod, thus restricting movement between the connected vertebrae. In multilevel procedures three or more pedicle screws may be utilized to span three or more vertebrae. The pedicle screw may be implanted as an assembled unit or in a modular fashion, in which the shaft 70 is implanted first leaving the shaft head 72 exposed above the pedicle. Thereafter, the receiver may be coupled to the shaft head at the appropriate time during the surgery. Utilizing a modular screw 68 when the minimally invasive facet release is to be performed may be advantageous in that the shaft may be implanted in the pedicle and used in place or the k-wire as an orientation marker, orienting the surgeon to the facet joint.

Figure 13:
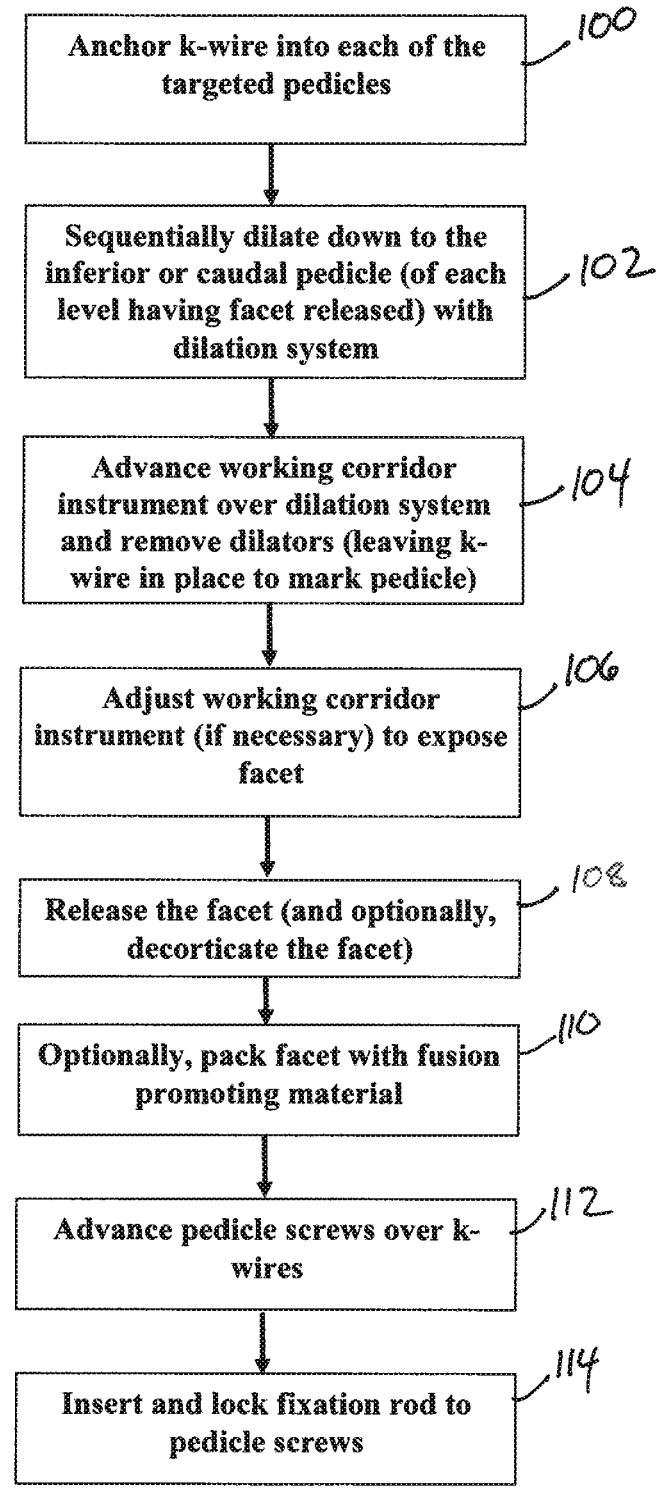
FIG. 13 is a flow chart illustrating steps in an example method of releasing a facet joint through minimally invasive access.

With reference to the flow chart of FIG. 13, one example embodiment of a method for minimally invasive facet release with posterior fixation is described. In step 100, a k-wire is anchored into the targeted pedicle of the superior and inferior vertebrae of each level to be fixated (facet release occurs adjacent the inferior or caudal pedicle). This may be accomplished using the pedicle access needle 58. For example, with the aid of a fluoroscope, an access needle is docked into each targeted pedicle. The stylet 62 may then be removed and a K-wire 46 anchored into each pedicle through the cannula 60 of the access needle 58, after which the cannula 60 are removed. In step 102, the dilation system 44 (or 52) including the initial dilator 48 (or 54) and one or more additional dilators 50 (or 56) are advanced sequentially over the k-wire 46 to the pedicle. Once the last dilator 50 (or 56) is advanced, the working corridor instrument 10 is advanced over the last dilator and the dilators are removed (step 104), leaving the k-wire in position within the working corridor and anchored in the pedicle.

If necessary, at step 106, the working corridor instrument 10 is adjusted to expose the facet. If the working corridor instrument is the tissue retractor 12, adjustment may include operating the retractor to move one or more of the plurality of blades 14 away from the other blades. In a preferred example, for example, the retractor is positioned such that the translating blade 14c is a medial blade and the blades 14a and 14b are cranial and caudal blades, respectively, and adjusting the retractor to expose the facet includes translating the retractor blade 14c medially. If the working corridor instrument is the access tube 36 adjustment may include shifting the access tube medially. Utilizing the sequential dilation system 54 (with matching access tube) may minimize the need for adjustment while still limiting the overall circumference of the access tube. The working corridor instrument 10 may be locked in place via a table mount or directly to the spine with fixation pin or k-wire if desired. Once the working corridor is set, the facet joint is released and decorticated (step 108). As described above, this release provides increased mobility to the motion segment allowing for better correction (e.g. disc height, lordosis, etc. . . . ). Once released, the facet may be packed with fusion promoting material (step 110). By way of example only, the fusion promoting materials may be one or more of BMP, demineralized bone matrix, collagen bone graft matrix, stem cell material, allograft cancellous bone, autograft bone, hydroxyapatite, coral and/or other highly porous substances. This will facilitate bone growth through the facet joint to help fuse the vertebrae in the corrected position. At step 112, the pedicle screw 68 is advanced over the k-wire and anchored into the pedicle. This may be done prior to removing the working corridor instrument (e.g. during a single level procedure) or after removing the working corridor instrument (e.g. during a multilevel procedure). A second pedicle screw 68 should also be advanced over the k-wire at the superior pedicle. The pedicle screws are preferably implanted with guide towers attached, as is known in the art, to facilitate subsequent rod passage. Finally, at step 114 a rod is connected to the pedicle screws and locked with locking caps 76. During a multilevel procedures, it may be preferable to complete step 100 for each pedicle prior to moving onto step 102. Thereafter, steps 102-110 may be completed sequentially for each pedicle prior to moving to the next pedicle to begin again at step 102. Finally, steps 112-114 can be completed at each pedicle after all desired facets have been released.

Figure 14:
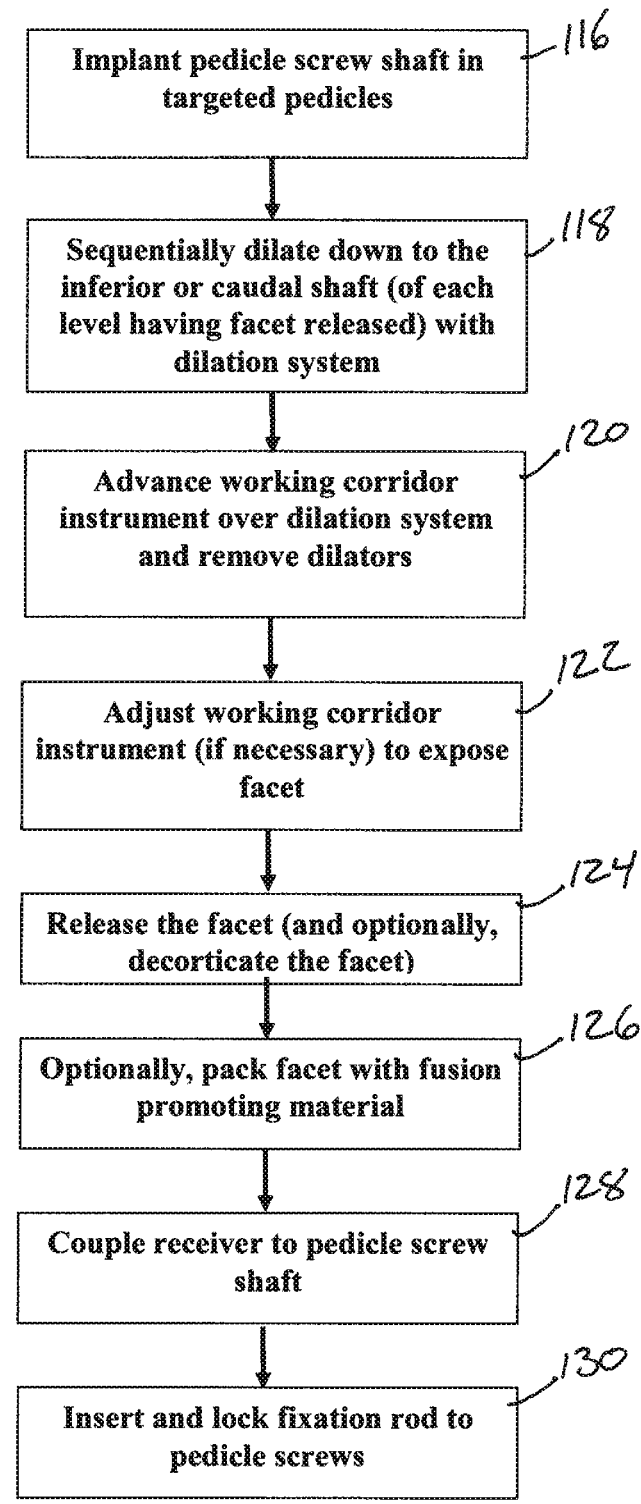
FIG. 14 is a flow chart illustrating steps in another example method of releasing a facet joint through minimally invasive access.

With reference to FIG. 14, another example embodiment of a method for minimally invasive facet release with posterior fixation is described. In step 116, a pedicle screw shaft 70 of a modular pedicle screw 68 is anchored into the targeted pedicle of the superior and inferior vertebrae of each level to be fixated (facet release occurs adjacent the inferior or caudal pedicle). This may be accomplished, for example, using the pedicle access needle 58. For example, with the aid of a fluoroscope, an access needle is docked into each targeted pedicle. The stylet 62 may then be removed and a K-wire 46 anchored into each pedicle through the cannula 60 of the access needle 58, after which the cannula 60 are removed. The shaft 70 may then be advanced directly over the k-wire 46 and anchored into the pedicle. Alternatively, one or more dilators may be advanced over the k-wire to create a path to the pedicle through which the shaft 70 is implanted. In step 118, the dilation system 44 (or 52) including the initial dilator 48 (or 54) and one or more additional dilators 50 (or 56) are advanced sequentially over the k-wire 46 to the shaft head 72. If a dilation system was used during placement of the anchor shaft 72, the dilators may be left in place and the initial dilator 48 (or 54) (and one or more of the additional dilators, if necessary) may be skipped and the additional dilators 50 (or 56) may be advanced over the dilators used for shaft placement. Once the last dilator 50 (or 56) is advanced (step 118), the working corridor instrument 10 is advanced over the last dilator and the dilators and k-wire are removed (step 120).

If necessary, at step 122, the working corridor instrument 10 is adjusted to expose the facet. If the working corridor instrument is the tissue retractor 12, adjustment may include operating the retractor to move one or more of the plurality of blades (as described above with reference to step 108). If the working corridor instrument is the access tube 36 adjustment may include shifting the access tube medially. Utilizing the sequential dilation system 54 (with matching access tube) may minimize the need for adjustment while still limiting the overall circumference of the access tube. The working corridor instrument 10 may be locked in place via a table mount or directly to the spine with fixation pin or k-wire if desired. Once the working corridor is set, the facet joint is released and, optionally, decorticated (step 124) and may be packed with fusion promoting material (step 126). At step 128, the receiver 74 is coupled to the shaft head 72. This may preferably be done prior to removing the working corridor instrument. The receivers are preferably implanted with guide towers attached, as is known in the art, to facilitate subsequent rod passage. Finally, at step 130 a rod is connected to the pedicle screws and locked with locking caps 76. During a multilevel procedures, it may be preferable to complete step 116 for each pedicle prior to moving onto step 118. Thereafter, steps 120-128 may be completed sequentially for each pedicle prior to moving to the next pedicle.

As described previously, and as will be evident to those skilled in the art, the above described methods boast several advantages over the prior art methods. While the invention is susceptible to various modifications and alternative forms, specific embodiments thereof have been shown and described by way of example. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein. For example, any of the features of a particular example described herein may be used with any other example described herein without departing from the scope of the present invention.

What is claimed is:

1. A method for minimally invasive release of a facet capsule during spinal surgery, comprising the steps of:
   advancing a k-wire into each of a superior pedicle and an inferior pedicle;
   advancing an initial dilator over the k-wire anchored in the inferior pedicle;
   advancing at least one additional dilator over the initial dilator;
   advancing a working corridor instrument over the at least one additional dilators the working corridor instrument comprising a tissue retractor having a translating medial blade, a cranial blade and a caudal blade;
   leaving the k-wire anchored in the inferior pedicle while removing each of the initial dilator and the at least one additional dilator to create an operative corridor with the distal end of the working corridor instrument defining an exposure over the inferior pedicle;
   adjusting the position of the working corridor instrument by moving the medial retractor blade away from at least one of the cranial retractor blade or the caudal retractor blade such that the exposure defined by the distal end of the working corridor moves to expose the facet joint;
   releasing the facet capsule;
   advancing a minimally invasive pedicle screw over the k-wire in the inferior pedicle and anchoring the pedicle screw into the inferior pedicle;
   advancing a minimally invasive pedicle screw over the k-wire in the superior pedicle and anchoring the pedicle screw into the superior pedicle;
   connecting the pedicle screw in the inferior pedicle and the pedicle screw in the superior pedicle with a connecting rod.

2. The method of claim 1, comprising the additional steps of decorticating the facet joint and packing the facet joint with fusion promoting materials.

3. A method for minimally invasive release of a facet capsule during spinal surgery, comprising the steps of:
   advancing a k-wire into each of a superior pedicle and an inferior pedicle;
   advancing an initial dilator over the k-wire anchored in the inferior pedicle;
   advancing at least one additional dilator over the initial dilator;
   advancing an access tube over the at least one additional dilator, the access tube having a proximal end, a distal end, and a longitudinal axis extending through the proximal and distal ends;
   leaving the k-wire anchored in the inferior pedicle while removing each of the initial dilator and the at least one additional dilator to create an operative corridor with the distal end of the access tube defining an exposure over the inferior pedicle;
   moving the access tube to reposition the longitudinal axis medially such that the exposure defined by the distal end of the access tube moves to expose the facet joint;
   releasing the facet capsule;
   advancing a minimally invasive pedicle screw over the k-wire in the inferior pedicle and anchoring the pedicle screw into the inferior pedicle;
   advancing a minimally invasive pedicle screw over the k-wire in the superior pedicle and anchoring the pedicle screw into the superior pedicle;
   connecting the pedicle screw in the inferior pedicle and the pedicle screw in the superior pedicle with a connecting rod; and
   locking the connecting rod to the pedicle screws.

4. The method of claim 3, comprising the additional steps of decorticating the facet joint and packing the facet joint with fusion promoting materials.

5. A method for minimally invasive release of a facet capsule during spinal surgery, comprising the steps of:

implanting the shaft of a modular pedicle screw into each of a superior pedicle and an inferior pedicle;

advancing a sequential dilation system down to the shaft in the inferior pedicle;

advancing an access tube over the sequential dilation system, the access tube having a proximal end, a distal end, and a longitudinal axis extending through the proximal and distal ends;

removing the sequential dilation system to create an operative corridor through the access tube with the distal end of the working corridor defining an exposure over the inferior pedicle;

moving the access tube to reposition the longitudinal axis medially such that the exposure defined by the distal end of the access tube moves to expose the facet joint;

releasing the facet capsule;

coupling a receiver to the shaft in the inferior pedicle;

coupling a receiver to the shaft in the superior pedicle;

connecting the receiver in the inferior pedicle and the receiver in the superior pedicle with a connecting rod; and locking the connecting rod to the pedicle screws.

6. The method of claim 5, comprising the additional steps of decorticating the facet joint and packing the facet joint with fusion promoting materials.

\* \* \* \* \*